(12) United States Patent
Fiorentino

(10) Patent No.: US 9,347,030 B2
(45) Date of Patent: May 24, 2016

(54) PHOTOBIOREACTOR

(71) Applicant: Julian Fiorentino, Miami, FL (US)

(72) Inventor: Julian Fiorentino, Miami, FL (US)

(73) Assignee: Julian Fiorentino, Miami, FL (US)

( * ) Notice: Subject to any disclaimer, the term of this patent is extended or adjusted under 35 U.S.C. 154(b) by 133 days.

(21) Appl. No.: 14/081,488

(22) Filed: Nov. 15, 2013

(65) Prior Publication Data

US 2014/0242687 A1   Aug. 28, 2014

Related U.S. Application Data

(60) Provisional application No. 61/771,002, filed on Feb. 28, 2013, provisional application No. 61/867,880, filed on Aug. 20, 2013.

(51) Int. Cl.
*C12M 1/00* (2006.01)
*C12M 1/12* (2006.01)

(52) U.S. Cl.
CPC ............... *C12M 21/02* (2013.01); *C12M 23/06* (2013.01); *C12M 29/08* (2013.01)

(58) Field of Classification Search
CPC ....... C12M 21/02; C12M 23/06; C12M 29/08
USPC ...................................................... 435/292.1
See application file for complete search history.

(56) References Cited

U.S. PATENT DOCUMENTS

| | | | |
|---|---|---|---|
| 5,151,347 A * | 9/1992 | Delente et al. ............. | 435/292.1 |
| 6,174,720 B1 | 1/2001 | Oxley et al. | |
| 8,003,379 B2 | 8/2011 | Goldman et al. | |
| 2003/0228684 A1 | 12/2003 | Burbidge et al. | |
| 2004/0055969 A1 | 3/2004 | Barnes | |
| 2009/0011492 A1 * | 1/2009 | Berzin ........................ | 435/292.1 |
| 2009/0199904 A1 * | 8/2009 | Babbitt et al. ............. | 435/292.1 |

(Continued)

FOREIGN PATENT DOCUMENTS

| WO | WO 2009/051479 A2 | 4/2009 |
|---|---|---|
| WO | WO 2010/076795 A1 | 7/2010 |

(Continued)

OTHER PUBLICATIONS

Carlozzi, Pietro, Closed Photobioreactor Assessments to Grow, Intensively, Light Dependent Microorganisms: A Twenty-Year Italian Outdoor Investigation, The Open Biotechnology Journal, 2008, pp. 63-72.

(Continued)

*Primary Examiner* — Nathan Bowers
*Assistant Examiner* — Timothy Barlow
(74) *Attorney, Agent, or Firm* — Feldman Gale, P.A.

(57) ABSTRACT

A photobioreactor system may include a one or more fluidly connectable tubes for growing or producing microorganisms or biomass such as microalgae. The system may include either a single tube loop or an array of tubes. A first fluid may be held in the tube or tubes, and an inlet port may be provided for introducing a second fluid into the tube or tubes. The tube or tubes may be arranged vertically so that the second fluid rises through the tube or tubes. An outlet port may be provided at the top of the tube or tubes to remove the second fluid. The second fluid may be recirculated through the system via inlet and outlet lines as well as a pump and a replaceable reservoir for holding the second fluid. Where there is an array of tubes, a single inlet and outlet line may be sued for each tube.

9 Claims, 6 Drawing Sheets

(56) References Cited

U.S. PATENT DOCUMENTS

| | | |
|---|---|---|
| 2010/0068779 A1* | 3/2010 | Wells .................... C12M 21/02 435/292.1 |
| 2010/0190236 A1 | 7/2010 | Delobel |
| 2011/0027875 A1* | 2/2011 | Cathcart .................... 435/292.1 |
| 2011/0159581 A1 | 6/2011 | Zhang et al. |
| 2012/0164712 A1 | 6/2012 | Ellem et al. |
| 2012/0184027 A1* | 7/2012 | Schuessler et al. ........ 435/292.1 |
| 2012/0252103 A1 | 10/2012 | Deane |
| 2012/0276633 A1* | 11/2012 | Gonzalez ............... C12M 21/02 435/257.1 |

FOREIGN PATENT DOCUMENTS

| WO | WO 2010/115412 A2 | 10/2010 |
|---|---|---|
| WO | WO 2011/035356 A2 | 3/2011 |
| WO | WO2011135375 * | 11/2011 |

OTHER PUBLICATIONS

Molina, E., Tubular Photobioreactor Design for Algal Cultures, Journal of Biotechnology, 2001, pp. 113-131, v. 92, Elsevier Science B.V.
Tubular Photobioreactors, Oligae, www.oliga.com/algae/cult/pbr/typ/tub/tub.html.

* cited by examiner

PHOTOBIOREACTOR

CROSS REFERENCE TO RELATED APPLICATIONS

This application claims the benefit of U.S. Provisional Application No. 61/771,002 filed Feb. 28, 2013 and U.S. Provisional Application No. 61/867,880 filed Aug. 20, 2013, the disclosures of which are each hereby incorporated herein by reference in their entireties.

FIELD OF THE INVENTION

This invention relates to the field of photobioreactors for growing or producing microorganisms or biomass such as microalgae.

BACKGROUND

As the atmospheric prevalence of carbon dioxide ($CO_2$) has increased over the previous decades, both governments and private entities have increasingly focused on new technologies for reducing and sequestering $CO_2$ and other anthropogenic emissions. This is especially true in the field of power or electricity generation where power plants operate through the combustion of fossil fuels, such as coal or natural gas, and emit significant amounts of $CO_2$ along with other greenhouse gases (GHG). Microorganisms such as microalgae and cyanobacteria (also known as blue-green algae) are well known to consume $CO_2$ as a part of their growth process. Thus, one area of $CO_2$ emission reduction research and technological advancement has been in the development of photobioreactors. A photobioreactor (PBR) may refer to a device or system that supports biological activity or growth and can rely on the use of a light source. Photobioreactors may be used to grow and cultivate microorganisms such as algae or cyanobacteria. Aiding in the microorganisms' growth process, a photobioreactor may be utilized for removal of $CO_2$ and GHG emissions from a power plant or other GHG emitting structure by capturing the emitted $CO_2$ or GHG and introducing it into the photobioreactor. The introduced $CO_2$ or GHG may thus assist the growth of the microorganisms, and the microorganisms' consumption of the flue gas thus operates to remove the GHG from the system, effectively filtering the gaseous emissions. Photobioreactors may also be similarly utilized in a variety of pollution control or treatment systems by relying on the microorganisms grown in the photobioreactor to capture or remove harmful particles, such as fertilizers from runoffs or effluent discharge in farms or chemicals in sewage. In addition to acting as a treatment system, photobioreactors offer the ability to effectively grow and harvest algae, which has many known beneficial uses. Various types of algae are known to be useful as a biofuel, fertilizer, or nutritional source, to name a few current uses for algae.

Presently known photobioreactors tend to be extremely complicated systems consisting of elaborate tube structures with a flow control mechanism for circulating water within the tube structures. In one example of a known photobioreactor, Burbidge et al. reportedly disclose a photobioreactor comprising an upstanding core structure; a plurality of substantially transparent tubes supportable by the core structure; flow means; and withdrawal means, where the plurality of transparent tubes are helically wound in parallel (U.S. Pub. Application No. 2003/0228684). In U.S. Pub. Application No. 2011/0159581, Another example of a known photobioreactor is reported by Zhang et al. to disclose an airlift circulation microalgae photoautotrophic-heterotrophic coupling photo bioreactor for wastewater treatments carbon emission mitigation. Furthermore, non-patent literature including "Closed Photobioreactor Assessments to Grow, Intensively, Light Dependent Microorganisms: A Twenty-Year Italian Outdoor Investigation," published in 2008 by the Open Biotechnology Journal, generally discusses the state of photobioreactor technology. Each of these references is incorporated herein, by reference, in its entirety.

These and other complex design features increase the cost to produce, install, and operate these known photobioreactors, while not necessarily improving their efficiency or production output. Additionally, due to the size and complication of the system, presently known photobioreactors are usually embodied in large, gaudy structures which have marginal utility beyond the structure's primary purpose as a photobioreactor. Moreover, large structures generally lack transportability. Accordingly, new photobioreactor systems and structures are desired to improve upon one or more of these deficiencies and expand photobioreactors' uses. The invention is directed to these and other important ends.

BRIEF SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In one embodiment of the disclosure, a photobioreactor system may include a first reactor tube having opposed upper and lower ends, an upper end tube having opposed first and second ends, with the first end of the upper end tube fluidly connectable to the upper end of the first reactor tube, a lower end tube having opposed first and second ends, with the first end of the lower end tube fluidly connectable to the lower end of the first reactor tube, and a second reactor tube having opposed upper and lower ends, with the upper end of the second reactor tube fluidly connectable to the second end of the upper end tube thereby fluidly connecting the upper end of the first reactor tube with the upper end of the second reactor tube through the upper end tube, with the lower end of the second reactor tube fluidly connectable to the lower end of the second reactor tube thereby fluidly connecting the lower end of the first reactor tube with the lower end of the second reactor tube, the fluidly connected first reactor tube, second reactor tube, lower end tube, and upper end tube defined as a photobioreactor loop in an installed position. The system may also include an inlet port provided proximate to the lower end tube for introducing a second fluid into the photobioreactor loop, an inlet line fluidly connectable with the inlet port and fluidly communicable with a second fluid source in order to fluidly connect the inlet port with the second fluid source, a pump fluidly communicable with the inlet line in order to move the second fluid from the second fluid source to the inlet port through the introduction line, and an outlet port provided proximate to the upper end tube for removing the second fluid from the photobioreactor loop. The upper end of the first reactor tube may be elevated above the lower end of the first reactor tube when the photobioreactor is in an installed position, and the upper end of the second reactor tube is elevated above the lower end of the second reactor tube when the photobioreactor is in the installed position. The system may also include an outlet line for fluidly connecting the outlet port with the second fluid source thereby establishing a closed system for circulating the second fluid between the second fluid source and the photobioreactor. The second fluid source may be a reservoir for holding the second fluid, and the reservoir may be interchangeable with a replacement reservoir. The first and second reactor tubes may each bend independently substantially elongate, and the upper and lower end tubes may be independently U-bends. The system may include a first fluid filling at least a portion of the photobioreactor loop, the first fluid having a greater density than the second fluid. The system may include at least one valve fluidly connected to the inlet port for regulating introduction of the second fluid into the photobioreactor loop. The system may include a split valve associated with the outlet port and an additive line fluidly connectable with the outlet port, with the spilt valve operable to control the fluid communication of the additive line and the exit line with the outlet port. The system may include a draining port provided proximate to the lower end for removing the first fluid from the photobioreactor loop, the draining port spaced at a distance from the inlet port. The system may include a plurality of baffles provided within the first reactor tube. The system may include a heat source provided within the photobioreactor loop in order to thermally urge fluid flow. The system may include a filter provided in fluid communication with the outlet port in order to prevent solid or semi-solid material from passing through the exit port. The first reactor tube may include a first side wall and a second side wall substantially enclosing the first side wall, the first and second side walls may also have different material properties for facilitating a photosynthetic process within the first reactor tube.

In another embodiment of the disclosure, a photobioreactor system may include a plurality of first reactor tubes each having opposed upper and lower ends, a plurality of upper end tubes, each upper end tube having opposed ends, one end of each upper end tube independently fluidly connectable to the upper end of one of the first reactor tubes, a plurality of lower end tubes, each lower end tube independently having opposed ends, one end of each lower end tube independently fluidly connectable to the lower end of one of the first reactor tubes, and a plurality of second reactor tubes, each second reactor tube having opposed upper and lower ends, the upper end of each second reactor tube independently fluidly connectable with one end of one of the upper end tubes in order to establish fluid communication between each second reactor tube and an adjacent first reactor tube at the upper ends, the lower end of each second reactor tube independently fluidly connectable with one end of one of the lower end tubes in order to establish fluid communication between each second reactor tube and an adjacent first reactor tube at the first and second reactor tubes' lower ends, creating a plurality of upper end tubes, lower end tubes, first reactor tubes, and second reactor tubes collectively defining a reactor tube array. The system may also include an inlet port provided proximate to the lower end of at least one first reactor tube for introducing a second fluid into at least a portion of the reactor tube array, an inlet line fluidly connectable with the inlet port and fluidly communicable with a second fluid source in order to fluidly connect the inlet port with the second fluid source, a pump fluidly communicable with the inlet line in order to move the second fluid from the second fluid source to the inlet port through the inlet line, and an outlet port provided proximate to the upper end of the at least one first reactor tube or the upper end of the adjacent second reactor tube for removing the second fluid from the at least a portion of the reactor tube array. Each upper end of the plurality of first reactor tubes may be independently elevated above its opposed lower end when the photobioreactor is in an installed position, and each upper end of the plurality of second reactor tubes may be independently elevated above its opposed lower end when the photobioreactor is in an installed position. The reactor tube array may be at least partially enclosed by a structure. The structure may be a wall of a building and the reactor tube array and be substantially concealed from a view taken from outside the building. The system may further include an outlet line for fluidly connecting the outlet port with the second fluid source thereby establishing a closed system for circulating the second fluid between the second fluid source and the reactor tube array. The second fluid source may be a reservoir for holding the second fluid, and the reservoir may be interchangeable with a replacement reservoir.

An additional embodiment of a photobioreactor system may include a plurality of first reactor tubes, each first reactor tube substantially elongate with opposed upper and lower ends, a plurality of upper end tubes, each upper end tube substantially dimensioned in a U-bend and having opposed ends, one end of each upper end tube fluidly connectable to the upper end of one of the first reactor tubes, a plurality of lower end tubes, each lower end tube substantially dimensioned in a U-bend and having opposed ends, one end of each lower end tube fluidly connectable to the lower end of one of the first reactor tubes, and a plurality of second reactor tubes, each second reactor tube substantially elongate with opposed upper and lower ends, the upper end of each second reactor tube fluidly connectable with one end of one of the upper end tubes in order to establish fluid communication between each second reactor tube and an adjacent first reactor tube at the upper ends, the lower end of each second reactor tube fluidly connectable with one end of one of the lower end tubes in order to establish fluid communication between each second reactor tube an adjacent first reactor tube at the lower ends, the plurality of interconnected upper end tubes, lower end tubes, first reactor tubes, and second reactor tubes may be collectively defined as a reactor tube array. The system may further include a first fluid containable within at least a portion of the reactor tube array, a plurality of inlet ports, each inlet port provided proximate to one of the lower end tubes in order to introduce a second fluid into the reactor tube array, at least one inlet line fluidly connectable to one or more inlet ports and fluidly communicable with a second fluid source in order to fluidly connect the one or more inlet ports with the second fluid source, a plurality of outlet ports, each outlet port provided proximate to one of the upper end tubes in order to remove the second fluid from the reactor tube array, at least one exit line fluidly connectable to one or more exit ports and fluidly communicable with the second fluid source in order to fluidly connect the one or more exit ports with the second fluid source thereby establishing a closed system between the reactor tube array and the second fluid source, and at least one pump fluidly communicable at a point in the closed system in order to generate a flow path of the second fluid between the second fluid source and the reactor tube array through the at least one introduction line and the at least one exit line. Each upper end of the plurality of first reactor tubes may be elevated above the opposed lower end when the photobioreactor is in an installed position, and each upper end of the plurality of second reactor tubes is elevated above the opposed lower end when the photobioreactor is in an installed position. The first fluid may have a greater density than the second fluid. The reactor tube array may be substantially enclosed within a structure. A single outlet line may be connectable with every outlet port and the second fluid source, and a single introduction line may be connectable with every inlet port and the second fluid source.

DETAILED DESCRIPTION

The following detailed description and the appended drawings describe and illustrate exemplary embodiments of the invention solely for the purpose of enabling one of ordinary skill in the relevant art to make and use the invention. As such, the detailed description and illustration of these embodiments are purely exemplary in nature and are in no way intended to limit the scope of the invention, or its protection, in any manner. It should also be understood that the drawings are not to scale and in certain instances details have been omitted, which are not necessary for an understanding of the present invention, such as details of fabrication and assembly.

Figure 1:
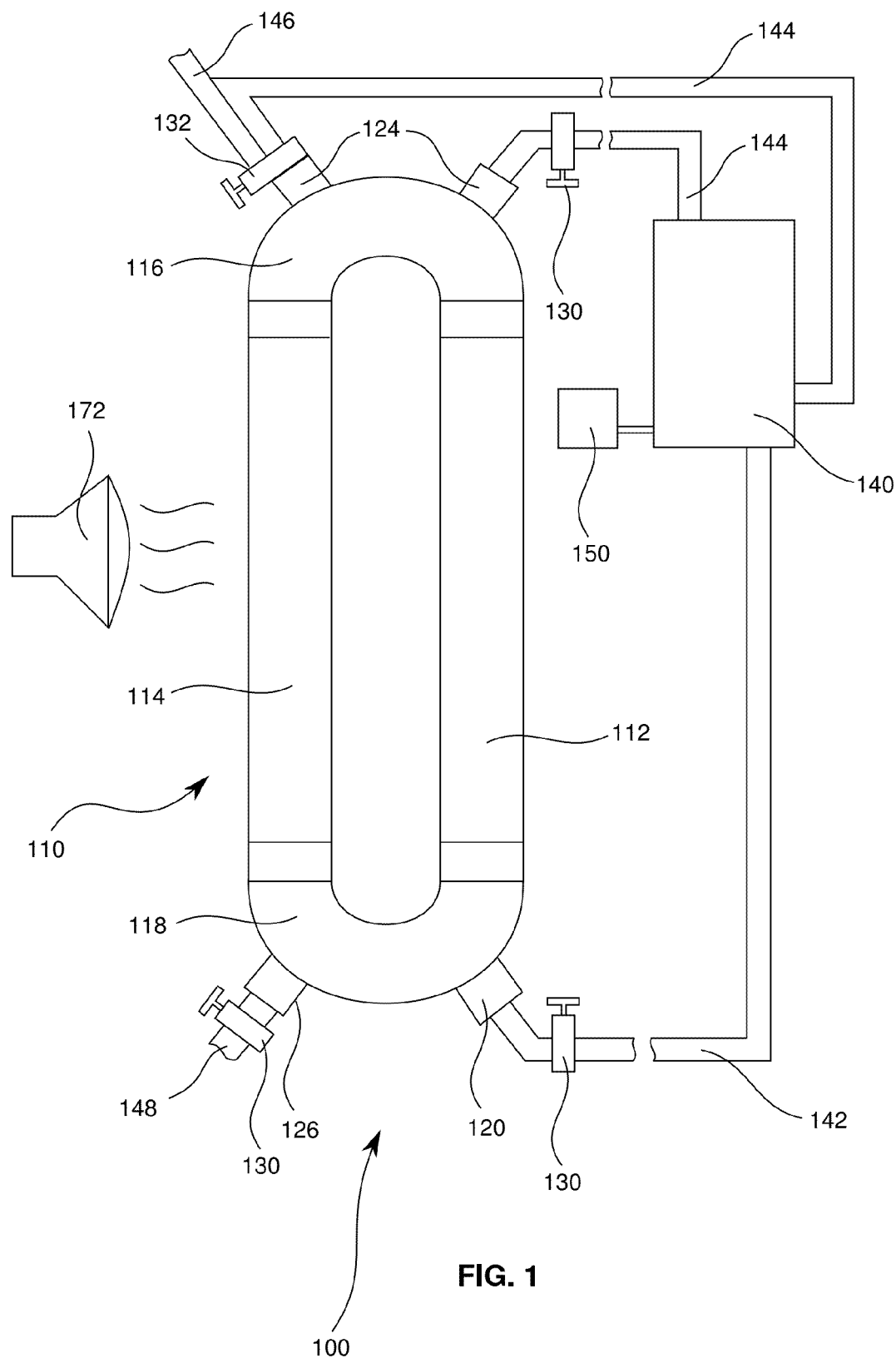
FIG. 1 illustrates a side view of an embodiment of a photobioreactor system in accordance with the disclosure.
Figure 2:
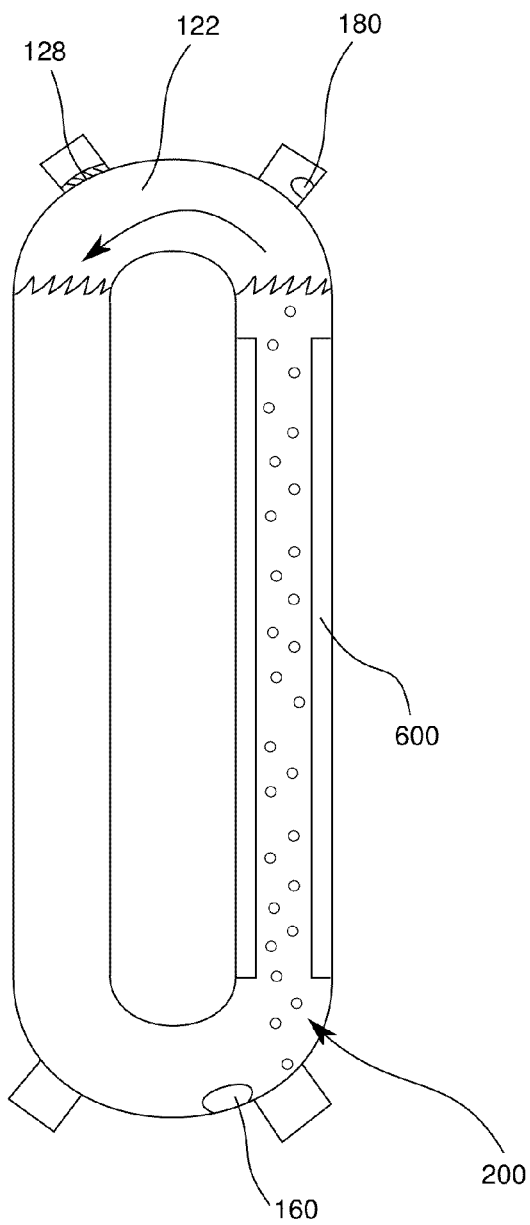
FIG. 2 illustrates a side cross-section view of an embodiment of a photobioreactor tube in accordance with the disclosure in order to show possible components on the inside of the photobioreactor tube.
Figure 3:
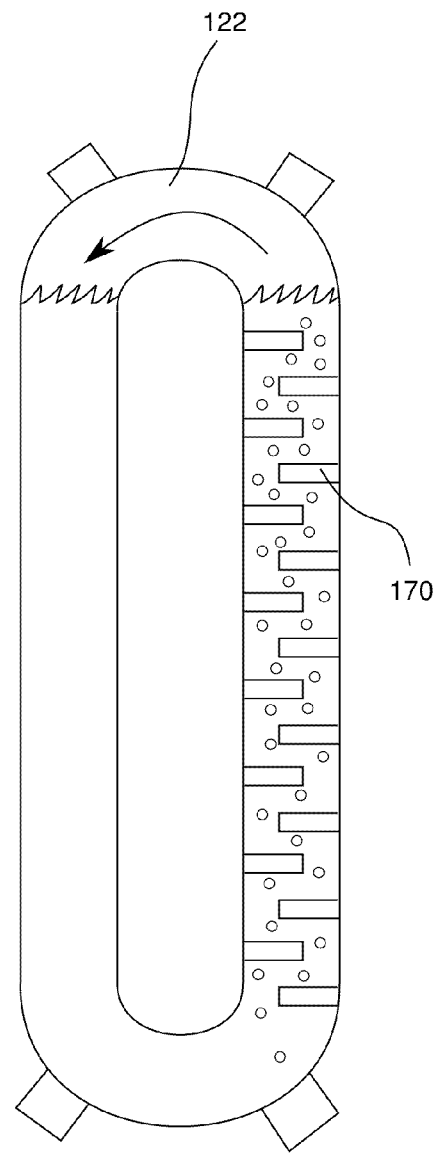
FIG. 3 illustrates a side cross-section view of an embodiment of a photobioreactor tube in accordance with the disclosure in order to show possible components on the inside of the photobioreactor tube.

With reference to FIGS. 1-3, an embodiment of a photobioreactor system 100 is provided for growing organisms such as algae, cyanobacteria, artemia, rotifers, or other single or multi-celled microorganisms. Photobioreactor system 100 may include a single photobioreactor tube 110 having a rising or up portion 112 and a falling or down portion 114. Embodiments of system 100 having one more tubes 110, such as the embodiment illustrated in FIG. 8 as well as embodiments including an array of interconnected tubes 110 as illustrated for example in the embodiments of FIGS. 4-7, are also described herein. Fluidly connecting rising portion 112 with falling portion 114 are first or upper end portion 116 and second or lower end portion 118. In FIG. 1, end portions 116, 118 are U bends respectively connecting the top and bottom ends of rising portion 112 with falling portion 114 to an enclosed system. It should be appreciated that tube 110 may be constructed with alternative orientations or dimensions in addition to the illustrated embodiment of FIG. 1 where rising and falling portions 112, 114 are substantially elongate tubes or tube sections and end portions 116, 118 are U bends. For instance, rising portion 112 and/or falling portion 114 may coil or bend at one or more angles, and rising portion 112 may or may not be similarly sized or dimensioned as falling portion 114. Additionally, end portions 116, 118 may be sized and dimensioned to have an orientation other than the U bend illustrated in FIG. 1 so long as first end portion 116 and second end portion 118 fluidly connect rising portion 112 and falling portion 114 thereby establishing a single photobioreactor tube 110 in order to function as described in accordance with an embodiment of the disclosure. Tube 110 may be manufactured with each portion 112, 114, 116, 118 as a single integral piece or, alternatively, portions 112, 114, 116, 118 may be separate pieces which may be connected together by known or to be developed means thereby assembling tube 110. In another embodiment, portions 112 and 116 may be dimensioned and shaped into an "L" or "J" that can be inverted, rotated and connected to simulate portions 114 and 118. An array of tubes 110, such as the embodiments of tube arrays 110 described herein and illustrated in FIGS. 4-7, may be quickly and cost efficiently produced through manufacturing methods such as but not limited to injection molding or three-dimensional printing, for instance or piecemealed. Tube 110 includes tube walls from which fluid 300 may be contained within, as described herein and illustrated in the embodiments illustrated in FIGS. 2 and 3. In some embodiments, all or a portion of tube 110 features a double wall design having an inner diameter wall for containing fluid 300 and an outer diameter wall surrounding the inner wall. A double wall design may add increased structural strength to tube 110 as well as permit tube 110 to be constructed from two separate materials, thereby permitting a variety of designs for controlling photosynthetic reactions as well as temperature regulation of the environment and material within tube 110. For instance, an outer wall of tube 110 may be constructed from a uniform material while an inner wall of tube 110 may be constructed from a first material at or proximate to first portion 112 and a second material at or proximate to second portion 114, with first and second materials having different thermal, luminous, electrical and/or photosynthetic properties.

Connected to lower end portion 118 is at least one gas introduction port 120 which may introduce a gas 200 into rising portion 112, as illustrated for instance in FIGS. 2 and 3. A valve 130 may be further provided so as to control the rate of gas 200 introduction. Valve 130 may operate through any known or to be developed mechanical or electrical means, including manual and automatic actuation as well as local and remote actuation, for instance as part of a controllable electrical system for operating photobioreactor system 100. In one embodiment, valve 130 may be a one-way valve permitting introduction of gas 200 in accordance with the disclosure and preventing backflow of gas 200 that may occur as a result of gravity. Various positions of introduction port 120 on lower end portion 118 are contemplated within the disclosure so long as gas 200 is introduced into rising portion 112 and not falling portion 114. Accordingly, in some embodiments introduction port 120 is positioned below or substantially below rising portion 112 so that gas 200 may naturally rise up and through rising portion 112 upon introduction into tube 110. Some embodiments may include a gas directing element (not illustrated), such as a miniature tube or a lower baffle in end portion 118, to facilitate alternative placements of gas introduction port 120 so that gas 200 may be introduced into rising portion 112 even though port 120 may not be provided at a position where gas 200 would naturally rise through rising portion 112 but for the utilization of a gas directing element. As one or more introduction ports 120 are contemplated within the disclosure, additional injection ports may be provided at intervals, for instance, along the rising portion 112 to facilitate consumption of different nutrients at different intervals. Alternatively, in an embodiment containing an array (FIGS. 4-7), injection of different gases at different individual interconnected rising portions 112 of a given array.

Provided within tube 110 is a fluid 300, which in one embodiment comprises water. Other fluids 300 or mixtures of fluids suitable for the growth or cultivation of algae or other microorganisms are contemplated within the disclosure. Fluids 300 can be supplied from any source, including but not limited to waste streams or intermittently placed within a system to stepwise alter liquid composition for further processing. In some embodiments, gas 200 is comprised of carbon dioxide, or any GHG or gaseous emission, which may be harvested for instance from fossil fuel emissions such as those from a gas or coal power plant. Atmospheric air is another contemplated gas 200. It is further contemplated that gas 200 may be a liquid having a lighter density than fluid 300 so that this lighter liquid 200 may rise through rising portion 112 in accordance with the disclosure. An introduced gas or liquid 200 may have its density further reduced by passing proximately by one or more heater elements, as described herein. It should be understood and appreciated by those of ordinary skill in the art that tube 110 should have at least a partial vertical orientation so that gas 200 rises through rising portion 112 of tube 110. In one embodiment, tube 110 may have a vertical or substantially vertical orientation. Frames or structures for maintaining tube 110's orientation are further described herein.

As shown in the illustrated embodiments of FIGS. 2 and 3, tube 110 may be only partially filled with fluid 300 so as to leave a head space or gap 122 in upper portion 116. In the illustrated embodiment, a sufficient quantity of fluid 300 is provided in tube 110 so that there is a space or gap between fluid 300 in rising portion 112 and fluid in falling portion 114. As a result of introduction and rising of gas 200, bubbles may be regularly introduced at the surface of fluid 300 on the side of upper portion 116 near rising portion 112. Additionally, as described in greater detail herein with regard to the growth and formation of microorganisms, a flow of fluid 300 occurs through rising portion 112. As a result of bubbles from gas 200 and fluid 300's flow, quantities of fluid 300 may be introduced into the head space or gap 122 and enter into falling portion 114 of tube 110. Certain embodiments of the disclosure contemplate tube 110 entirely or nearly entirely filled with fluid 300. Some embodiments contemplate partially filing tube 110 with fluid 300 thereby creating a head space or gap 122, thereby reducing, mitigating, and/or substantially eliminating backflow, swirling or other similar fluid phenomena which may destruct fluid 300 flow as described herein. Fluid 300 flow may also be regulated or adjustable by other known or to be developed devices for regulating fluid flow placed in or proximate to tube 110.

In order to temporarily contain gas 200, or optionally to separate gas and liquid from line 142, a reservoir or tank 140 may be included in system 100. An introduction line or hose 142 may be provided between tank 140 and introduction port 120, and valve 130 may regulate the flow of gas 200 introduction. Gas 200 may be removed from gap 122 in upper end portion 116 through one or more exit ports 124. Exit port 124 may be connected to tank 140 through an exit line or hose 144. In embodiments where tube 110 is filled or nearly filled with fluid 300, thereby eliminating gap 122, one or more exit ports 124 may be provided to remove fluid 300 from tube 110 in order to facilitate circulation of fluid 300 within system 100. A screen 128 may also be provided in or proximate to exit port 124 in order to block biomaterial, introduced nutrients, or other particles from exiting tube 110. Similarly, screen 128 may be placed at any port 120, 124, 126 in order to prevent or substantially block material from leaving tube 110 or system 100. One or more ports 120, 124 may be controlled by a split or dual line valve 132 in order to facilitate multiple lines or hoses communicating with the controlled port 120, 124. Dual source valve 132 may be a "Y" valve or a multi-port valve. In the illustrated embodiment, exit port 124 positioned over falling portion 114 includes a dual valve 132, with an exit line 144 as well as an additive line 146 connected to, and in fluid communication with, exit port 124. Dual valve 132 may, thus, operate to switch the function of port 124. In one operation mode, dual valve 132 may operate to permit gas 200 to escape from exit port 124 through exit line 144. In a second operation mode, dual valve 132 may operate to place additive line 146 in fluid communication with tube 110 in order to permit introduction of nutrients or other additives into tube 110 as may be desired. Alternately a dual valve 132 can be positioned at introduction port 120 an additional introduction line (not illustrated) may be utilized for supplemental gas or low density fluid addition into tube 110, which may include a variety of gases for any number of uses including environmental control or optimization of growth. Any additive may be introduced proximately over falling portion 114 so that they may enter circulation, in accordance with the fluid flow and gas 200 introduction described herein, throughout the entirety of the microorganisms growing in tube 110, particularly at the lower end of rising portion 112. Providing a dual valve 132 and additive line 146 to be in communication with exit port 124 proximately over rising portion 112 is also contemplated within the disclosure. Some or all of the valves 130, 132 described herein may be pressure or release valves having in order facilitate pressurization and safety in system 100 by purging to but not limited to the environment, reservoir 140, or another reservoir (not illustrated).

Valves 130, 132 may be individual or a manifold, remote, or part of each respective port 120, 124, 126 valve 130, 132 is connected to or associated with, and may be manufactured with or separately from their respective port 120, 124, 126 and from tube 110. A filter 128 may be further provided in or proximate to one or more ports 120, 124, 126 as well as in or proximate to one or more valves 130, 132. Filter 128 may effectively eliminate or reduce unintentional removal of biomass or nutrients from tube 110 or unintentional introduction of material mixed with gas 200 which should not be introduced into tube 110

By connecting lines 142, 144 to reservoir 140, a closed system may be established for moving gas 200 between reservoir 140 and tube 110. A pump 150 may be provided in fluid communication with the closed system in order to move gas 200 throughout the system. In one embodiment, pump 150 may include a variable speed motor in order to vary the volume of gas 200 flowing through photobioreactor system 100. By controlling the speed or force of which gas 200 is introduced, optimal algal growth conditions may be maintained, for instance by assuring fluid 300 flow is sufficiently strong to circulate nutrients while maintaining the flow as laminar which may be preferable to a turbulent flow. System 100 may be able to introduce captured gaseous emissions, including for example, $CO_2$, by collecting the emissions in reservoir 140 and introducing reservoir 140 into system 100. Gaseous plant emissions can also be directly connected to port 120 overriding or as opposed to the collection of gas 200 in 140, and pump 150 may be utilized to circulate plant emissions or, in another embodiment, to take plant emissions introduced in addition to or in place of gas 200 and to begin a recirculation process leading plant emissions to reservoir 140. When the available nutrients has been effectively converted by the microorganisms, reservoir 140 may be replaced or switched with another reservoir containing collected emission gases. In another embodiment of system 100, reservoir 140 is replaced by open atmospheric air thereby creating an open system 100. Pump 150 may then be utilized to introduce air as gas 200 into system 100. Introduction line 142 or other lines connected to port 120 may deliver emissions from or proximate to an emission source, such as the coal stacks of a power plant. A line or tube may be placed at or proximate to the bottom of reservoir 140, such as where introduction line 142 is provided in the illustrated embodiment. Thus, fluid 300 which may have been pumped from tube 110 through exit line 144 may be reintroduced into tube 110 through introduction line 142. Alternatively, a separate drain line (not illustrated) may be connected to reservoir 140 so as to drain introduced fluid 300 from reservoir 140. Alternatively in the case that an array is long enough to allow for enough residence and processing time the exit line may pass through a filter/screen 128 into another PBR array containing another type of microorganism for a stepwise processing of fluid/gas. Multiple pumps 150 and multiple tanks 140 per system 100 are also contemplated within the disclosure.

A heating element or thermal regulatory device 160 may be further provided in tube 110 in order to encourage fluid flow as well as to potentially affect the environment within tube 110 so as to facilitate growth conditions for the microorganisms inside tube 110. For instance, thermal source 160 may be placed at the lower end of rising portion 112 so as to increase flow of fluid 300 upwards through rising portion 112 through the introduction of heat and decrease in density of fluid 300 around element 160 facilitating vertical motion. Thermal source 160 may also be used to control both by increasing or decreasing the temperature of fluid 300 and/or tube 110 so as to promote or encourage optimal growth conditions.

Tube 110 may further include additional internal structure for encouraging or promoting the mixing of fluid 300 during its fluid flow, thereby circulating or mixing introduced nutrients. In one embodiment, one or more baffles 170 may be included in at least a portion of tube 110, for instance in rising portion 112 as provided in the illustrated embodiment. Ridges along tube 110 walls may also be provided, which may for instance be sized and dimensioned to be circular, helical or spiral within tube 110.

In order to encourage and facilitate microorganism growth, a light source 172 may be provided so as to direct or emit light towards system 100 and, more particularly, tube 110. Light is a necessary component of the photosynthetic process. In some embodiments, natural sunlight may be utilized to grow the microorganisms. Light source 172, however, may be incorporated to emit light at a specific spectrum or a specific light wavelength in order to facilitate microorganism growth which may be more responsive to wavelengths other than those naturally provided in sunlight. Additionally, light source 172 permits microorganism growth at night. So that the microorganisms may receive light, tube 110 may be constructed from material having photosynthetic properties. In some embodiments, this may be a clear or translucent material, such as plastic or glass, but in some embodiments a non-translucent photosynthetic material, such as photosynthetic metals like aluminum, may be utilized. Combination of translucent and opaque materials is also considered to regulate the light/dark cycles, or the specific wavelengths of light that penetrate the tubes. Light source 172 may be any known or to be developed light emitting device including, for instance, lasers, light emitting diodes, bulbs, or a fiber optic network with an on/off cycle that is indeterminate and variable.

As described herein, system 100 thus operates as a recirculating microorganism cultivation apparatus for growing a biomass, such as microalgae, which in some embodiments may grow as algal bloom 600 along the walls of tube 110, as illustrated for instance in FIG. 2. In order to determine when microorganism growth has peaked and/or is ready for harvesting, a sensor 180 may be provided as part of system 100. Any number of sensor(s) 180 may be utilized for monitoring the quantity or quality of one or more substances within system 100 such as biomass concentration, chlorophyll concentration, dissolved nutrients and dissolved gases 200. Sensors(s) 180 may thus assist an operator of system 100 to determine when algae should be harvested or reservoir 140 should be removed or changed. There are a variety of positions which one or more sensors 180 may be utilized. Sensor(s) 180 may be provided in or proximate to reservoir 140 as well as in, on or proximate to tube 110. Sensor(s) 180 may also, for instance, be provided for within or in proximity to any of the one or more valves 130, 132 or ports 120, 124, 126 included in an embodiment of system 100. In one embodiment, sensor(s) 180, valves 130, 132, and/or ports 120, 124, 126 may be connectable to an electrical control system, which may include a processor (not illustrated) and a display (not illustrated) for controlling at least one valve 130, 132 or port 120, 124, 126 in addition to pump 150 and light source 170. A control system may also include memory, data logging and transmission means (not illustrated) for recording sensor(s) 180 readings as well as control history of the system 100. Control system may automatically control system 100 in response to sensor(s) 180 readings and may operate to activate or deactivate pump 150, valve 130, 132 or port 120, 124, 126 as is appropriate based on sensor(s) 180 readings. Control system may also be manually controlled through a user and the processor may alert the user of changes in sensor(s) readings so that the user may act accordingly in operation of system 100.

When it is time to harvest the microorganisms, fluid 300 may be removed through a draining port 126 and a draining tube or line 148 provided on or proximate to lower end region 118. Removal of fluid 300 may be through gravitational force or, in one embodiment, pump 150 may be utilized to pressurize tube 110 in order to force water out of tube 110, for instance by reversing the operating direction of pump 150 and forcing gas 200 through exit port 124 positioned at the upper end 116 of tube 110. A screen or filter 128 may be provided in or proximate to either port 124 or an associated valve 130 in order to trap microorganisms which may unintentionally flow into port 124 with draining fluid 300. Once fluid 300 is drained, a second or draining fluid may be introduced into tube 100 for forcibly removing the microorganisms. This draining fluid, which may be water in certain embodiments, may be introduced for instance through feeding line 146 and may be sufficiently pressurized to force microorganisms, such as algal bloom 600, from the walls of tube 110. The draining fluid and removed microorganisms may then flow into draining port 126 and through drain line 148 thereby collecting the grown microorganisms. Cultivation can be on a batch basis or on a continuous basis depending on the application of system 100. Also any number of subsequent microorganism processing steps to retrieve the produced materials is considered to be within the ambit of this disclosure.

Figure 4:
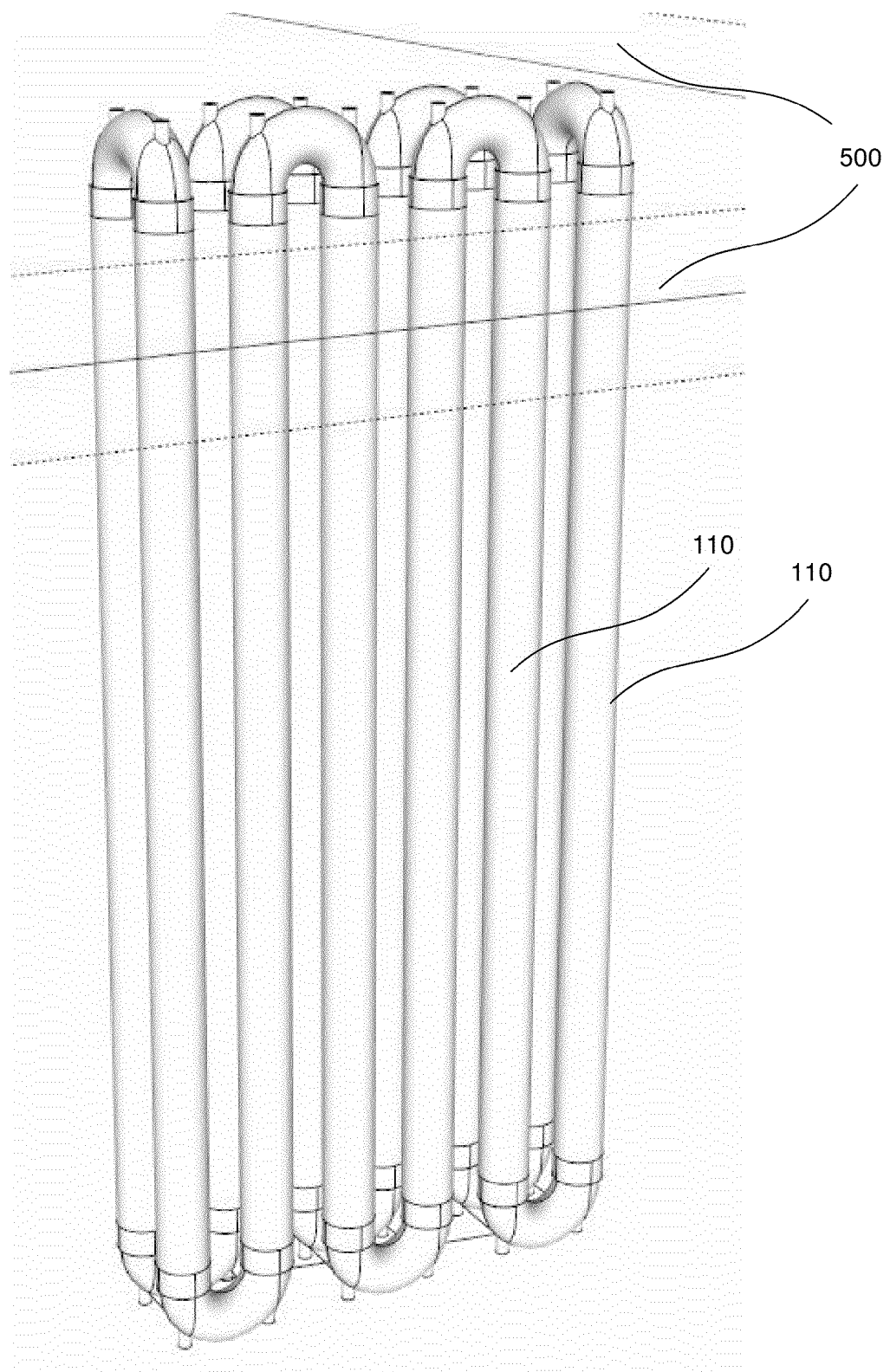
FIG. 4 illustrates a side perspective view of an embodiment of multiple interconnected photobioreactor tubes as an array.
Figure 5:
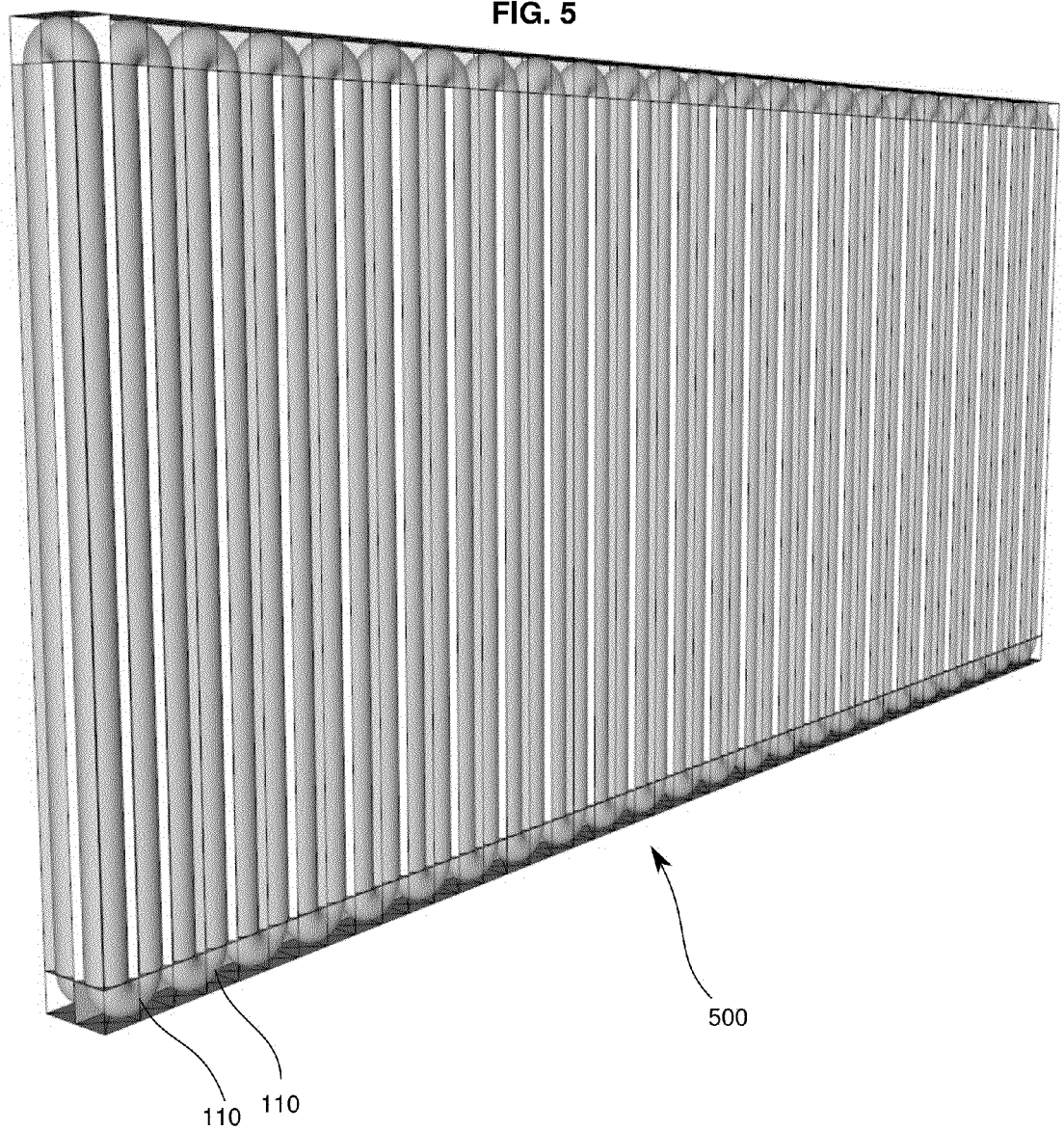
FIG. 5 illustrates a side perspective view of an embodiment of multiple interconnected photobioreactor tubes as an array and embedded in an embodiment of a structure in accordance with the disclosure.

With reference now to FIGS. 4-8, system 100 may comprise a plurality of tubes 110 arranged in an array. As illustrated in FIGS. 4 and 5, tube 110 array may feature a series of tubes 110 aligned or substantially aligned into a row or rows. This alignment may accordingly permit tube 110 array to be provided within a structure 500, such as the wall of a building.

Figure 6:
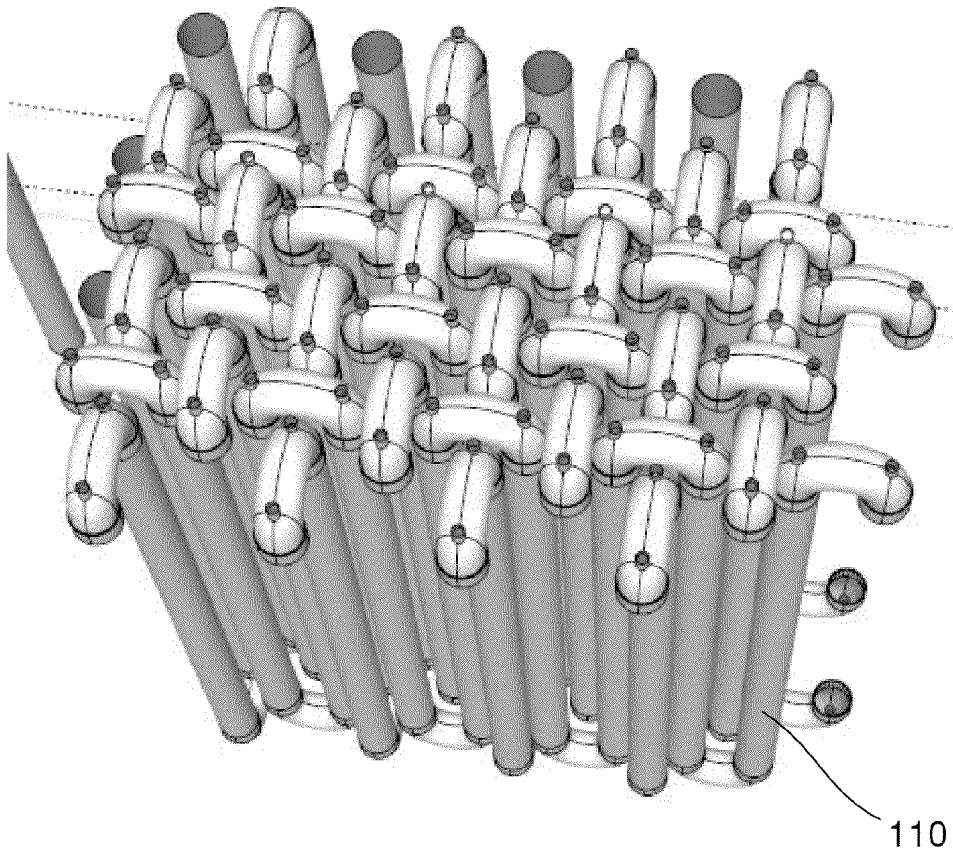
FIG. 6 illustrates a top perspective view of an embodiment of a photobioreactor tube interlocking array in accordance with the disclosure.

The remainder of system 100, such as reservoir 140 and pump 150, may also be provided within structure 500 or, alternatively, may be provided at remote location from structure 500 connected to tube 110 array through lines 142, 144, as individually routed lines, or a single designed conduit. As shown in FIG. 6, tubes 110 may also be placed in a cross-hatch or intersecting arrangement, where some tubes 110 are angled out of phase with respect to other tubes 110 creating an interlocking pattern where the spaces between one set of portions 112 and 114 coincide with the continuities of another set of portions 112 and 114.

Figure 7:
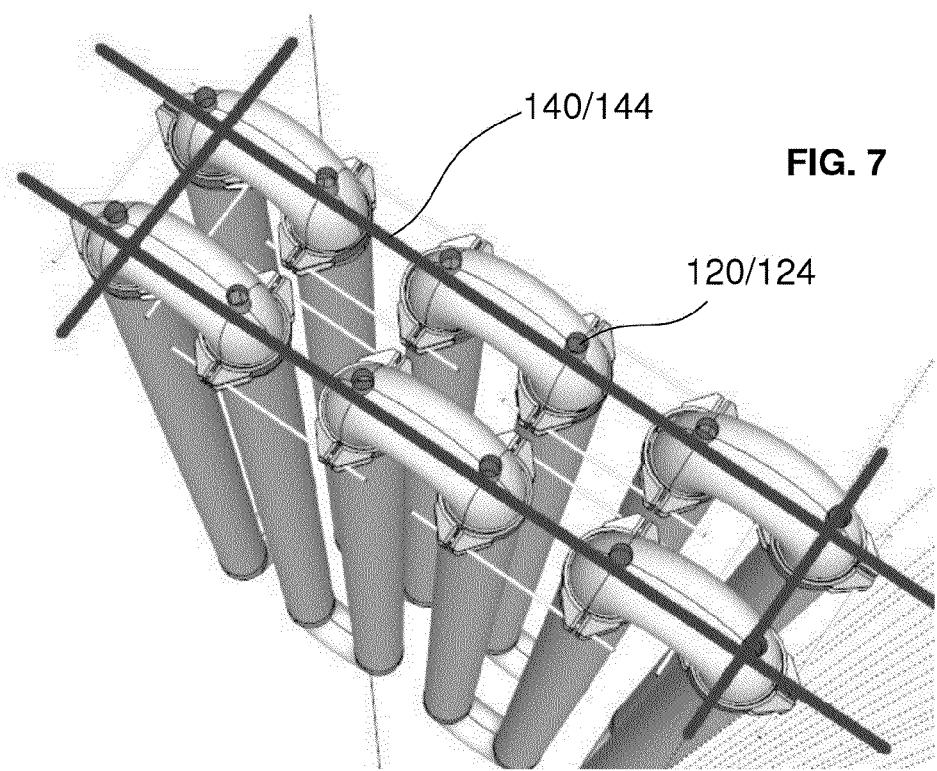
FIG. 7 illustrates a top perspective view of an embodiment of a photobioreactor tube array with supports to facilitate the embodiment of the array to be embedded in a structure in accordance with the disclosure.

FIG. 7 illustrates one arrangement of lines 142/144 connected to ports 120/124 for an array of tubes 110. Here, lines 142/144 may connect to ports 120/124 for multiple tubes 110. Lines 142/144 may then be in communication with a single pump 150 thereby creating a closed system for the entire array. Valves 130 may then be utilized to maintain a constant pressure in each tube 110 of the array thereby accommodating for pressure drops between each tube 110. This arrangement lowers manufacturing costs by reducing material required in addition to facilitating the arrangement of tube 110 array so that it may compactly fit within structure 500.

Certain embodiments of system 100 including an array of tubes 110, such as those illustrated in FIGS. 4-7, may include tubes 110 a plurality of rising portions 112 connected to an adjacent falling portion 114, as well as one or more falling portions 114 connected to an adjacent rising portion 112. In these embodiments, a single fluidly connected tube 110 contains a plurality of rising portions 112 and falling portions 114 interconnected by end portions 116, 118. An upper end portion 116 may fluidly connect a first rising portion 112 with a first portion, and a lower end portion may fluidly connect first rising portion 112 with a second lower end portion 114. This is in contrast to other embodiments, such as the embodiment illustrated in FIG. 8, where an array of tubes 110 may include tubes 110 having only one rising portion 112 and one falling portion 114 mutually connected by end portions 116, 118. It should be understood and appreciated that system 100 may comprise an array of both types of tubes 110, that is a first tube type having multiple rising and falling portions 112, 114 interconnected, such as the embodiments illustrated in FIGS. 4-7, and a second tube type having one rising and one falling portion 112, 114, such as the embodiment illustrated in FIG. 8.

Figure 8:
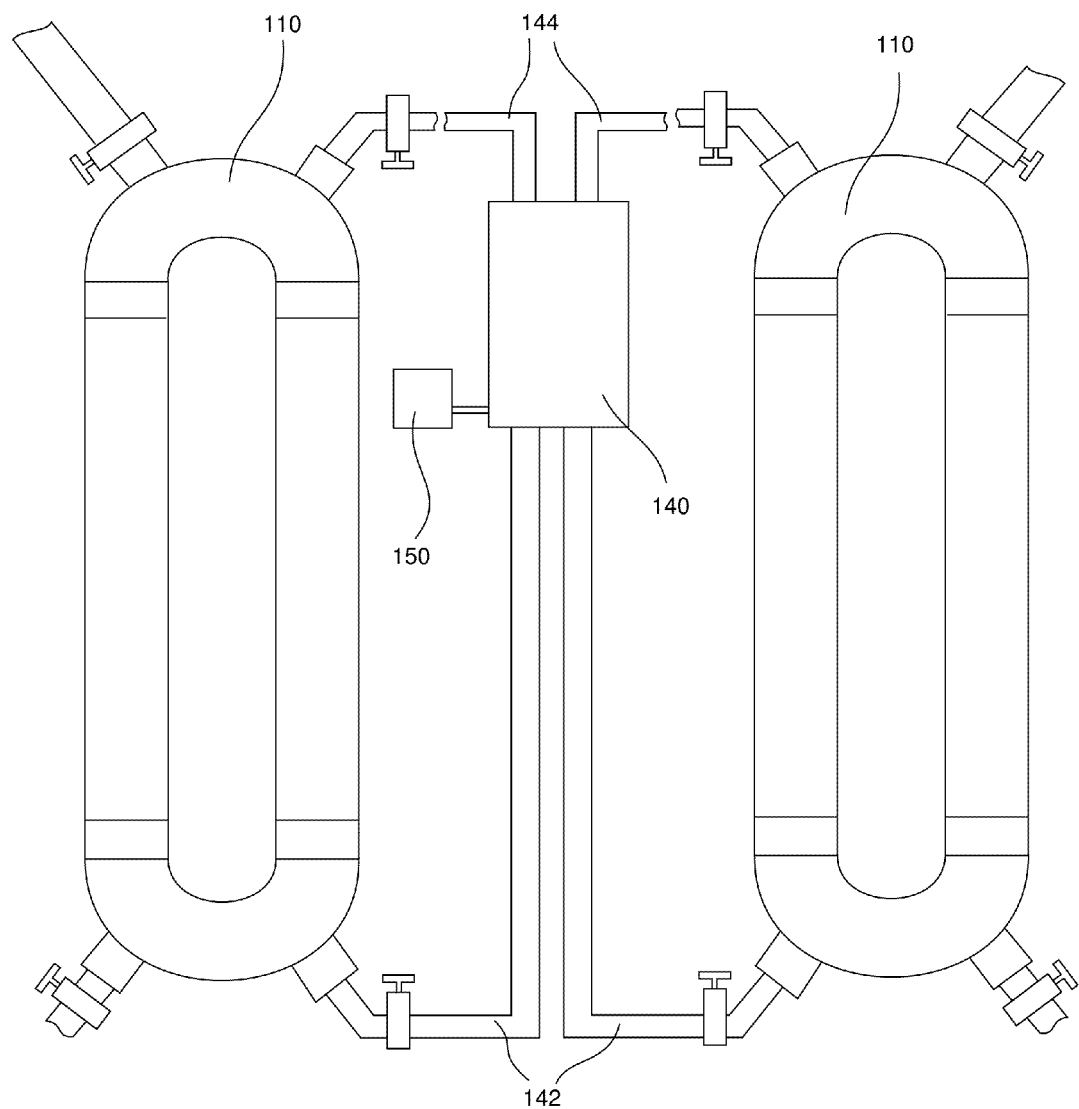
FIG. 8 illustrates a side view of an embodiment of a photobioreactor system having a plurality of photobioreactor tubes in accordance with the disclosure.

FIG. 8 shows one embodiment of system 100 where a single reservoir 140 and pump 150 may be utilized for an array of tubes 110. Lines 142/144 may commonly lead from respective tubes 110 into a common reservoir 140 which is associated with a pump 150. In this way, gas 200 may be cycled through multiple tubes 110 thereby increasing the efficiency of system 100 and reduction of $CO_2$ emissions contained in gas 200. It should be understood and appreciate that a single reservoir 140 and pump 150 may be utilized in tube 110 arrays having multiple rising and falling portions, such as those embodiments illustrated in FIGS. 4-7.

In one embodiment of system 100, an array of tubes 110 may be assembled inside an enclosed mobile vehicle, such as a trailer or any transportable container. The system 100 may then be easily transported to any nutrient or emission source, with connections to ports 120, 124, 126 made at exterior walls of the mobile vehicle for integration to an existing structure providing the required gas and liquid. In some embodiments, all ports 120, 124, 126 and pumps 150 and additional components of system 100 can be included in the enclosed transport container providing immediate, remote and/or self-sufficient implementation.

The components described herein may be manufactured or produced through any known or to be developed methods of manufacturing including, but not limited to, forging, injection molding, CNC, laser cutting, or three dimensional printing etc.

The descriptions set forth above are meant to be illustrative and not limiting. Various modifications of the invention, in addition to those described herein, will be apparent to those skilled in the art from the foregoing description. Such modifications are also intended to fall within the scope of the concepts described herein. The disclosures of each patent, patent application and publication cited or described in this document are hereby incorporated herein by reference, in their entireties.

The invention illustratively disclosed herein suitably may be practiced in the absence of any element which is not specifically disclosed herein. The invention illustratively disclosed herein suitably may also be practiced in the absence of any element which is not specifically disclosed herein and that does not materially affect the basic and novel characteristics of the claimed invention.

What is claimed:

1. A photobioreactor system comprising:
a plurality of photobioreactor loops grouped into a first set of photobioreactor loops and a second set of photobioreactor loops, each photobioreactor loop including
a first reactor tube having opposed upper and lower ends,
an upper end tube having opposed first and second ends, the first end of the upper end tube directly connectable to the upper end of the first reactor tube,
a lower end tube having opposed first and second ends, the first end of the lower end tube directly connectable to the lower end of the first reactor tube, and
a second reactor tube having opposed upper and lower ends, the upper end of the second reactor tube directly connectable to the second end of the upper end tube thereby fluidly connecting the upper end of the first reactor tube with the upper end of the second reactor tube through the upper end tube, the lower end of the second reactor tube directly connectable to the lower end of the first reactor tube thereby fluidly connecting the lower end of the first reactor tube with the lower end of the second reactor tube,
wherein the connected first reactor tube, second reactor tube, lower end tube, and upper end tube has a raceway configuration in an installed position;
a plurality of inlet ports, each inlet port provided either on one of the lower end tubes or on the first reactor tube proximate to the connected lower end tube for introducing a second fluid into at least a portion of each photobioreactor loop;
at least one inlet line fluidly connectable with each inlet port and fluidly communicable with a second fluid source in order to fluidly connect the inlet port with the second fluid source;
a pump fluidly communicable with the at least one inlet line in order to move the second fluid from the second fluid source to the plurality of inlet ports through the at least one inlet line; and
a plurality of outlet ports, each outlet port provided proximate to the upper end tube for removing the second fluid from each photobioreactor loop,
wherein the upper end of the first reactor tube is elevated above the lower end of the first reactor tube when the photobioreactor is in an installed position, and the upper end of the second reactor tube is elevated above the lower end of the second reactor tube when the photobioreactor is in the installed position, and wherein the first and second set of photobioreactor loops are arranged in a cross hatched orientation such that each photobioreactor loop of the first set of photobioreactor loops is aligned oriented in a first direction and each photobioreactor loop of the second set of photobioreactor loops is aligned in a second direction.

2. The photobioreactor system of claim 1, wherein each photobioreactor loop of the first set of photobioreactors loops is separated from an adjacent photobioreactor loop of the first set of photobioreactors loops by a photobioreactor of the second set of photobioreactors, and wherein each photobioreactor of the second set of photobioreactors is separated from an adjacent photobioreactor of the second set of photobioreactors by a photobioreactor of the first set of photobioreactors.

3. The photobioreactor system of claim 1, wherein the second fluid source is a reservoir for holding the second fluid, and the photobioreactor system further comprising:

an outlet line connectable between the outlet port and the reservoir, wherein the second fluid is circulate-able through the reservoir, the inlet line connected to the inlet port, the at least one of the plurality of photobioreactor loops, the outlet line connected to the output port, and back through the reservoir.

4. The photobioreactor system of claim 3 further comprising a replacement reservoir for storing replacement second fluid, wherein the reservoir is interchangeable with the replacement reservoir thereby introducing the replacement second fluid into the at least one of the plurality of photobioreactor loops and removing a processed fluid stored in the reservoir, the processed fluid having been modified as part of a photosynthetic process.

5. The photobioreactor system of claim 1, further comprising a structure having at least one wall, wherein the plurality of photobioreactor loops are at least partially enclosed within the at least one wall.

6. The photobioreactor system of claim 1, wherein each of the plurality of inlet ports is provided adjacent to the first reactor tube for introduction of the second fluid into one of the first reactor tubes while substantially eliminating introduction of the second fluid into any of the second reactor tubes.

7. The photobioreactor system of claim 1 further comprising a heat source provided within at least one of the plurality of photobioreactor loops in order to thermally urge fluid flow.

8. The photobioreactor system of claim 1 further comprising further comprising a plurality of baffles provided within at least one of the plurality of photobioreactor loops.

9. The photobioreactor system of claim 1 further comprising a first fluid filling at least a portion of at least one of the plurality of photobioreactor loops, the first fluid having a different density than the second fluid.

* * * * *